(12) United States Patent
Lewis et al.

(10) Patent No.: US 6,254,552 B1
(45) Date of Patent: Jul. 3, 2001

(54) INTRA-CORONARY RADIATION DEVICES CONTAINING CE-144 OR RU-106

(75) Inventors: Robert E. Lewis, Milford, NH (US); Prahlad R. Singh, Arlington, MA (US); Gerald P. Tercho, Lexington, MA (US); Paul R. Walsh, Harvard, MA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/164,730

(22) Filed: Oct. 1, 1998

Related U.S. Application Data (60) Provisional application No. 60/060,805, filed on Oct. 3, 1997.

(51) Int. Cl.[7] ..................................... A61N 5/00
(52) U.S. Cl. ............................................. 600/603
(58) Field of Search ............................... 600/1–8

(56) References Cited

U.S. PATENT DOCUMENTS

| | | | |
|---|---|---|---|
| 3,811,426 | * 5/1974 | Culver et al. .......................... 600/3 |
| 5,163,896 | * 11/1992 | Suthanthiran .......................... 600/8 |
| 5,342,283 | * 8/1994 | Good ....................................... 600/8 |
| 5,833,593 | * 11/1998 | Liprie ..................................... 600/3 |
| 5,857,956 | * 1/1999 | Liprie ..................................... 600/7 |
| 5,871,436 | * 2/1999 | Eury ....................................... 600/3 |
| B1 5,199,939 | 8/1998 | Dake et al. . | |

FOREIGN PATENT DOCUMENTS

| 9848851 | 11/1998 | (WO) . |
|---|---|---|
| 9848852 | 11/1998 | (WO) . |

OTHER PUBLICATIONS

Furukawa et al., JP 62254773, (*Chemical Abstracts*, No. 109, XP002095177, 1988).
Furukawa et al., JP 62254773, (*Chemical Abstracts*, No. 109, Dec. 1988).
Furukawa et al., JP 62254773, (*Derwent Abstracts*, 1987).
Teirstein et al., *N. Engl. J. Med.*, 336:1697–1703 (Jun. 1997), Catheter Based Radiotherapy to Inhibit Restenosis After Coronary Stenting.

* cited by examiner

*Primary Examiner*—Samuel G. Gilbert
(74) *Attorney, Agent, or Firm*—Peter L. Dolan (57) ABSTRACT

An intra-coronary radiation devices containing Ce-144 or Ru-106 deposited onto a wire and coated with a biocompatible material and methods of making and using the same.

23 Claims, 1 Drawing Sheet

INTRA-CORONARY RADIATION DEVICES CONTAINING CE-144 OR RU-106

This application claims the benefit of U.S. Provisional Application No. 60,060,805, filed Oct. 3, 1997.

FIELD OF THE INVENTION

This invention relates generally to intra-coronary radiation devices containing Ce-144 or Ru-106 and methods of using and making the same.

BACKGROUND OF THE INVENTION

The effectiveness of radiation in preventing restenosis following angioplasty was demonstrated in a 1995–1996 study conducted by Paul Teirstein of Scripps Clinic in which sources prepared from Ir-192 were used in patients previously receiving balloon angioplasty and stent implantation (Teirstein et al., *N. Engl. J. Med.*, 336:1697–1703 (1997)). The study showed that in patients receiving the radioactive source treatment, the restenosis rate dropped to 16.7% in the radiation treated group versus 53.6% of the patients in the "placebo" group not receiving radiation.

One of the problems with the current intra-coronary radiation devices (ICRD) is the exposure of the source to the medical personnel. For example, currently after administration of the Ir-192 source, the operators and physicians have to leave the treatment room to avoid getting an excessive dose.

Sr-90 and P-32 are among the other ICRD sources currently in clinical trials. Both of these sources has serious limitations. Sr-90 is problematic due to its high toxicity in the event of source and catheter rupture in the patient. P-32 may have a less than optimum beta energy to provide the proper dose profile, at least in larger calcified plaque occluded arteries.

It is desirable to develop an ICRD which can provide a 4:1 dose at 1 mm and 4 mm respectively in the artery, have a sufficiently long half-life to allow multiple patient use at minimum cost, and have minimum radiation exposure to the medical personnel.

SUMMARY OF THE INVENTION

Accordingly, one object of the present invention is to provide a novel intra-coronary radiation device.

It is another object of the present invention is to provide a method for treating arterial disease, which comprises administering to a host in need of such treatment a therapeutically effective intra-coronary radiation device.

It is another object of the present invention to provide a method of preparing an intra-coronary radiation device.

These and other objects, which will become apparent during the following detailed description, have been achieved by the inventors', discovery that an intra-coronary radiation device containing either Ce-144 or Ru-106 should be an economical and safe means of treating arterial disease.

BRIEF DESCRIPTION OF THE DRAWINGS

The invention is illustrated by reference to the accompanying drawings below.

DETAILED DESCRIPTION OF PREFERRED EMBODIMENTS

Figure 1:
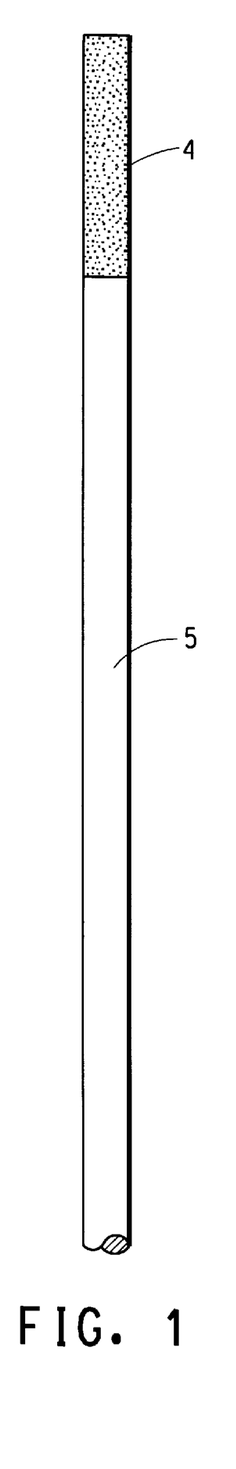
FIG. 1 shows a catheter guide wire (5) having a radioactive segment (4).
Figure 2:
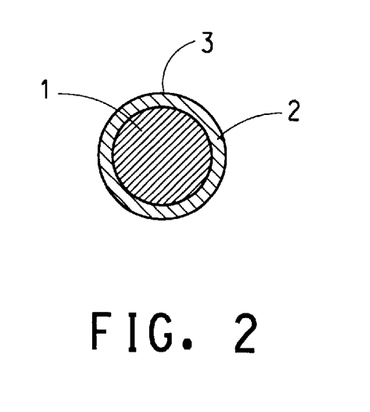
FIG. 2 is a cross-sectional view of the radioactive segment showing the wire (1), having radiation source layer (2) deposited or absorbed on the wire (1), and a biocampatible layer (3) sealing the radiation source layer (2) and wire (1).

In a first embodiment, the present invention provides a novel device for intra-coronary radiation therapy, comprising:

(a) a wire;

(b) a radiation source deposited or adsorbed onto the wire, wherein the radiation source is Ce-144 or Ru-106; and, (c) a first biocompatible material sealing the radiation source and wire.

In another preferred embodiment, the radiation source is Ru-106.

In a preferred embodiment, the radiation source is Ce-144.

In another preferred embodiment, the wire is metal and is selected from: zirconium, titanium, aluminum, nickel, copper, graphite wire, 304 stainless steel or copper plated stainless steel.

In a more preferred embodiment, the wire is 304 stainless steel or copper plated stainless steel.

In another preferred embodiment, the radiation source is electrolytically deposited onto the wire.

In another preferred embodiment, the radiation source is deposited onto the wire via an oxidation-reduction process.

In another preferred embodiment, the radiation source is adsorbed onto the wire.

In another preferred embodiment, the first biocompatible material is selected from: polyimide, polyamide, polyvinyl chloride, gold, nickel, and heat shrink tubing.

In another more preferred embodiment, the first biocompatible material is heat shrink tubing.

In an even more preferred embodiment, the first biocompatible material is polyethylene terephthalate.

In another preferred embodiment, the intra-coronary radiation device is attached to a guide wire, wherein the guide wire is capable of being inserted into a catheter.

In another more preferred embodiment, a second biocompatible material encapsulates the intra-coronary radiation device attached to the guide wire.

In another even more preferred embodiment, the second biocompatible material is heat shrink tubing.

In a further preferred embodiment, the second biocompatible material is polyethylene terephthalate.

In a second embodiment, the present invention provides a novel device for intra-coronary radiation therapy, comprising:

(a) a wire, wherein the wire is an extruded wire, comprising:

(ai) a radiation source selected from Ce-144 and Ru-106; and, (aii) a metal selected from copper, aluminum, sliver, gold and nickel.

In another preferred embodiment, the radiation source is Ce-144 and the metal is aluminum.

In another preferred embodiment, the radiation source is Ru-106 and the metal is aluminum.

In another preferred embodiment, the wire is prepared by extruding a blended mixture of the radiation source and the metal, both of which are in the form of a powder.

In another preferred embodiment, the device further comprises:

(c) a biocompatible material encapsulating the wire.

In a third embodiment, the present invention provides a novel device for intra-coronary radiation therapy, comprising:

(a) a tube;

(b) a bead located within the tube; and,
(c) a radiation source complexed to the bead, wherein the source is Ce-144 or Ru-106.

In another preferred embodiment, the radiation source is Ce-144.

In another preferred embodiment, the radiation source is Ru-106.

In a fourth embodiment, the present invention provides a novel process for making an intra-coronary radiation device (ICRD), comprising:
(a) depositing a radioactive source onto a metal wire segment, wherein the radioactive source is Ce-144 or Ru-106; and,
(b) sealing the deposited radioactive source with a first biocompatible material.

In another preferred embodiment, the radiation source is Ru-106.

In another preferred embodiment, the radiation source is Ce-144.

In another more preferred embodiment, step (a) is performed by adsorption, deposition via reduction-oxidation, or electroplating.

In another even more preferred embodiment, step (a) is performed by adsorption.

In another even more preferred embodiment, step (a) is performed by deposition via reduction-oxidation.

In another even more preferred embodiment, step (a) is performed by electroplating.

In a further preferred embodiment, Ce-144 is electroplated onto the wire from an organic solution.

In an even further preferred embodiment, the organic solution, comprises: $^{144}Ce(COOCF_3)_3$ and a solvent selected from methanol, ethanol, isopropyl alcohol, and MeCN.

In a still further preferred embodiment, $^{144}Ce(COOCF_3)_3$ is prepared by contacting $^{144}CeCl_3$ with $(CF_3CO)_2O$ and $CF_3COOH$.

In another more preferred embodiment, step (b) is performed by:
(bi) electroplating the wire from step (a) with a metal,
(bii) applying a polymeric coating to the wire from step (a) and subsequently curing the polymeric coating, or
(biii) inserting the wire from step (a) into heat shrink tubing and subsequently heat shrinking the tubing.

In another even more preferred embodiment, step (b) is performed by: (bi) electroplating the wire from step (a) with a metal selected from gold and nickel.

In another further preferred embodiment, the metal is gold.

In another even more preferred embodiment, step (b) is performed by: (bii) applying a polymeric coating to the wire from step (a) and subsequently curing the polymeric coating.

In another further preferred embodiment, the polymeric coating is a polyimide.

In another even more preferred embodiment, step (b) is performed by: (biii) inserting the wire from step (a) into heat shrink tubing and subsequently heat shrinking the tubing.

In another further preferred embodiment, the heat shrink tubing is polyethylene terephthalate.

In another more preferred embodiment, the process further comprises:
(c) attaching the sealed wire to a guide wire, wherein the guide wire is capable of being inserted into a catheter.

In another even more preferred embodiment, the process further comprises:
(d) applying a second biocompatible material to the attached sealed wire from step (c).

In another further preferred embodiment, the second biocompatible material is heat shrink tubing.

In an even further preferred embodiment, the heat shrink tubing is polyethylene terephthalate.

In a fifth embodiment, the present invention provides a novel method for treating a diseased artery, comprising: inserting into a catheter an intra-coronary radiation device (ICRD) attached to a guide wire, wherein the ICRD, comprises:
(a) a wire;
(b) a radiation source deposited or adsorbed onto the wire, wherein the radiation source is Ce-144 or Ru-106; and,
(c) a biocompatible material encapsulating the radiation source and wire.

Description

Typical intra-coronary radiation device (ICRD) wire sources have dimensions which vary from 1 to 5 cm in length and 0.1 to 0.35 mm in diameter. Preferably the dimensions will be from 2 to 4 cm by 0.15 to 0.3 mm and more preferably 3 cm in length and 0.20 to 0.25 mm in diameter. The diameter preferably is 0.20, 0.21, 0.22, 0.23, 0.24 or 0.25 mm in diameter.

For intra-coronary radiation therapy, the radioactive wire matrix will be attached to a guide wire which will be introduced into the patient's diseased artery via a catheter tube. The radioactive wire segment should be attached mechanically with a slip or interference fit male/female connection secured either by laser welding or with a biocompatible adhesive such as polyisocyanurate. After the radioactive wire and guide wire have been secured together, it may be preferable to coat this device with a biocompatible material such as heat shrink tubing or other similar materials.

Radiation Sources

The two radiation sources considered for the present intra-coronary radiation devices are Ce-144 and Ru-106. The penetrating beta radiation of 3 to 3.5 MeV is emitted by the 17.3 minute half life praseodymium-144 daughter, and the 30 second half life rhodium-106 daughter respectively, which are each in secular equilibrium with their parent nuclides. The daughter nuclides decay with the half lives of the parent nuclides, therefore the beneficial beta radiation dosage follows the parent decay pattern of the 285 day half life for Ce-144 and the 1.02 year half life for Ru-106.

The expected source content will be about 6 to 7 mCi of Ce-144 or Ru-106, although greater amounts of nuclide may be employed to shorten patient exposure time and extend the life of these devices. These wire sources when attached to the guide wire can be inserted into catheter's that are closed on one end hence they do not come in contact with blood and consequently do not need to be sterile and can be reused in another patient.

Wire

The wire can be composed of a variety of metals, such as zirconium, titanium, aluminum, nickel, copper, graphite; alloys of zirconium, titanium, or nickel, brass, constantan, aluminum alloy, magnesium alloy, stainless steel, and other metals, alloys and intermetallics which possess sufficient springiness equivalent to 304 stainless steel.

Source Deposition

The radiation source can be attached to the wire via a number of processes, including electrolytic deposition, reduction-oxidation deposition, or chemical adsorption.

Electrolytic Deposition

A preferred way of attaching Ce-144 or Ru-106 is through electrolytic deposition. The nuclides may be in their elemental form or as oxides, phosphates, sulfates, or other ionic or molecular forms, directly, or as complexed with ligands such as trifluoroacetates, acetonates, chlorides, oxalates, citrates, tartrates, amines, acetates, cyanides, nitrosylates, halides and other chelates or ligands as know to those of skill in the art. Preferably, Ce-144 is in its elemental form or is in its trifluoroacetate, phosphate or chloride form. Preferably, Ru-106 is in elemental form.

For electrodeposition of Ce-144, an organic solution of $^{144}$Ce(COOCF$_3$)$_3$ can be used. The wire used is, preferably, 304 stainless steel, stainless steel with a plated copper undercoat or flash, titanium, titanium alloy, or nickel, alloy, more preferably, 304 stainless steel or stainless steel with a plated copper undercoat or flash. A preferable biocompatible coating of Al, Au or Pt can be subsequently applied thereby keeping the radioactivity from oxidation or from being "naked" or "exposed".

$^{144}$Ce(COOCF$_3$)$_3$ can be prepared by reacting anhydrous $^{144}$Cerium (III) chloride with (CF$_3$CO)$_2$O and CF$_3$COOH. It is prefeable that about 1.5 equivalents of (CF$_3$CO)$_2$O and CF$_3$COOH are used. It is preferred that the mixture be heated to reflux for about 3 hours in an anhydrous atmosphere. $^{144}$Ce(COOCF$_3$)$_3$ can the be recovered by removal of the liquid components. Various organic solvents can be used, including methanol, ethanol, isopropyl alcohol, and MeCN, preferably methanol.

The anhydrous trifluoroacetate salt of $^{144}$Cerium can also be prepared by reacting the anhydrous metal chloride with a solution of silver trifluoroacetate in a dry solvent (e.g. dry acetonitrile). Subsequent evaporation of the solvent under pressure should provides the anhydrous trifluoroacetate.

Electrodeposition of Ru-106 can be achieved using ruthenium chloride in a plating bath. Nitrosyl sulfamic acid can be used to convert the chloride to ruthenium nitrosyl sulfamate. This material can then be plated onto a desired wire using known plating methods (e.g., barrel plating). It is preferred to protect the plated Ru-106 with a biocompatible material, such as gold.

Another process for cerium involves electroplating of Ce-144 in its elemental form out of a molten salt bath at about 900° C. The bath constituents are, preferably, KCl, NaCl and CeCl$_3$. Preferably, the anode used is a graphite cell, the cathode is a stainless steel or beryllium-copper alloy wire segment. The plating current may be from 10 to 30 amps per cm$^2$. The biocompatible material is preferably, electroless nickel overplate, gold overplate or heat shrink tubing.

Chemical Deposition

Another preferred method of attaching the nuclide to the wire is by chemical deposition as a red-ox process. This process uses a reductant (e.g., sodium hypobromite) to reduce the nuclide, preferably Ru-106, in the presence of the wire. A variety of reductants can be used, such as nitrite, sulfite, hypophosphite, halogens such as iodide and hypohalites such as hypobromite, H$_2$ gas with nickel, platinum or other catalysts, zinc metal, amalgamated zinc, metallic sodium in organic solvents, lithium aluminum hydride and other metal hydrides, and other common reductants. Preferred reductants are sodium or potassium hypohalites or sodium or potassium hypophosphite.

Adsorption

Another preferred method for attaching the nuclide to the wire is via adsorption onto the wire matrix. Adsorption is based on the chemical affinity of ionic cerium or ruthenium for inorganic substances such as titanium oxide, phosphate, or sulfate, zirconium oxide, phosphate, or sulfate, tungstates, molybdates, or on the ability of elemental or molecular forms of ruthenium or cerium to deposit directly on the active metal surface of the wire.

Adsorption requires the wire to have been preconditioned with an oxidant such as nitric acid, sulfuric acid, phosphoric acid, nitrates, phosphates, sulfates, bromine and other elemental halogens, iodic and other halogen acids, picric acid, other organic oxidizing acids and their salts, metallic oxide salts such as sodium or potassium molybdate, or sodium or potassium tungstate. Preferred oxidants include phosphoric acid, nitric acid, sulfuric acid, phosphate salts, and nitrate salts. More preferred oxidants include phosphoric acid or nitric acid. Preconditioned means that the metallic surface of the wire is converted through an oxidative process to a film or layer of oxide, phosphate or sulfate.

Biocompatible Material

After depositing or adsorbing the radiation source onto the wire, the wire is then sealed (i.e., encapsulated) with a biocompatible material. The purpose behind sealing the wire and source is to prevent leakage of the source into the patient. This is desirable even if the wire is inserted into a closed catheter, in case of a leak developing in the catheter. The thickness of the biocompatible material layer will depend upon the material chosen. One of ordinary skill in the art would recognize the layer would need to be of sufficient thickness to prevent leakage of the source if the device is exposed to body fluids.

A wide variety of materials such as metals and polymers may be used. One of the purpose for encapsulating the source and wire is to prevent leaching of the radiation source into the patient. Thus, a sufficient coating would be one that allows the intra-coronary radiation device to be placed inside a patient's artery, via a catheter or some other appropriate delivery method, for a therapeutically effective time without an undesirable release of the radiation source.

An example of a biocompatible material is a thin coating of gold, platinum, rhodium, silver or any of the noble metals, including alloys such as gold-platinum, platinum-rhodium, platinum-iridium and similar durable coatings used in the jewelry industry. Preferably the coating is gold or platinum, more preferably, gold. The thickness of the metal coating is preferably from $5 \times 10^{-5}$ to $13 \times 10^{-5}$ mm.

Another example of a biocompatible material is a thermoplastic polymer coating such as polyvinyl chloride, polyvinyl acetate, polyethylene, polypropylene, or any other medical grade polymer resistant to radiation, and applied through a hot dip or coating process. These polymeric coatings can be air or catalytically cured.

Still another example of a biocompatible material is a thermoset polymer coating such as epoxy, polyurethane, polyimide, polytetrafluoroethylene (e.g., Teflon®), or polyamide (e.g., Nylon®), or any other medical grade thermoset polymers resistant to radiation, preferably, a polyimide. These coatings would be applied using a wire coating process as employed commercially for electrical wire or through a dip method. Coatings of this type can be cured by heating, ultraviolet light, using a catalyst, or using chemical hardeners.

A further example of a biocompatible material is a polymeric or similar sleeve or tubing such as polyethylene, polypropylene, polyvinyl chloride, polyvinyl acetate, polyimide, teflon or any medical grade tubing resistant to radiation. Such a tube or sleeve would be applied using a mechanical insertion of the active wire matrix and the ends would be sealed using heat, laser or mechanical sealing process.

Materials such as polyethylene terephthalate (PET), polytetrafluoroethylene, polyvinylidine chloride, or other types of heat shrink tubing may be applied to the wire matrix similarly to the tubing materials described above. Preferably, the biocompatible material is PET or heat shrink tubing, more preferably, PET. Heat can then be applied to shrink the tubing. It may also be useful to apply a second heat shrink layer after attaching the intra-coronary radiation device to the guide wire.

Wire Alloy

The intra-coronary radiation device can be a wire formed as an alloy or intermetallic by one of the following processes. The cerium and ruthenium or their oxides, phosphates, sulfates, or other ionic materials, may be physically blended with metal powder in a commercially available blending device and then extruded, formed or drawn, using an extrusion die or similar commercially available equipment. The metal powders can be any of the following: copper, aluminum, gold, silver, nickel, or any other metals which are, or have been used to fabricate extruded wire in the industry.

Beads

The intra-coronary radiation device can also be formed using organic or inorganic ion exchange beads, or beads containing chelating groups. Beads comprised, for example, of styrene-divinyl benzene, containing functional groups such as quaternary amine groups, sulfonic acid groups, ethylene diamine tetra acetic acid groups, peptide groups, imido groups, or other functional groups are used to complex the cerium or ruthenium nuclides in their anionic or cationic a forms and immobilize them. The loaded beads are then sealed by firing at high temperature, or chemically, as with a furan resin and ethylene oxide to prevent leaching of the nuclides from the bead matrix.

The sealed beads are then loaded into thin wall tubing such as stainless steel, titanium, aluminum, nickel or other medically compatible metal tubing, or any alloy such as titanol, monel, or any alloy of the aforementioned metals, or any medically compatible polymeric tubing including the polymeric materials noted previously. The loaded tubing sections are then mechanically attached to the catheter guide wire for the intended application.

A preferred method is to use polystyrene beads with sulfonic acid functional groups, for example, Dowex-50 cation exchange beads. The beads are loaded with Ce-144 chloride out of a 0.1 to 0.5 M HCl solution, dried, then carbonized in a furnace at a temperature of about 1100° C. for 1 hour. The carbonized beads are then loaded into a tube segment, preferably, stainless steel, having the same dimensions and slip fit or interference fit modified end as the wire matrix segment. The open end of the tube through which the beads are loaded is then sealed, preferably with a laser. This tube segment is attached to a guide wire using a slip/interference fit and laser or adhesive attachment as described above with the wire matrix segment.

Other features of the invention will become apparent in the course of the following descriptions of exemplary embodiments which are given for illustration of the invention and are not intended to be limiting thereof.

EXAMPLES

The preparation of representative intra-coronary devices according to the invention is described in further detail below with reference to the following specific, but non-limiting examples.

Example 1

Electrodeposition of $^{144}$Ce from a $^{144}$Ce(COOCF$_3$)$_3$ organic solution.

A Ce-144 "source" for use as an intra-coronary radiation device can be prepared by electrodeposition of Ce-144 from a $^{144}$Ce(COOCF$_3$)$_3$ organic solution. The wire used is 304 stainless steel.

To 3.0 g of anhydrous $^{144}$Cerium (III) chloride is added 6 ml each of (CF$_3$CO)$_2$O and CF$_3$COOH (the total of both the acids equals about 1.5× the equivalent amount of acids required to react with anhydrous $^{144}$CeCl$_3$). The mixture is heated under reflux for ~3 hr. in an anhydrous atmosphere. The solution is evaporated in a rotary evaporator and analyzed.

Electrodeposition can be achieved onto a metal or alloy, directly or using a base plate from an electrolytic bath at various temperatures (RT to 50° C.) and various current densities (0.5–30 A.dm$^{-2}$). A platinum plate is used as the anode. Solubility and electrical conductivity of the $^{144}$Ce(CF$_3$COO)$_3$ in various organic solutions such as MeOH, EtOH, i—PrOH, MeCN is determined prior to the electrodeposition procedure to identify the ideal media to be used for the bath. The dieletric constant of a particular solvent is expected to play a large part in determining the solubility of in $^{144}$Ce(CF$_3$COO)$_3$ a particular solvent.

Upon completion of this electrodeposition process, biocompatible coating of Al, Au or Pt can be applied using a similar procedure. For e.g. An Al(COOCF$_3$)$_3$ can be prepared using the above stated method and can be electrodeposited from a Al(COOCF$_3$)$_3$- MeOH bath.

Example 3

Preparation of Ce-144 ICRD by adsorption.

1. Condition the wire segments, which are pure zirconium for this example, with a hot solution of phosphoric acid containing 10% nitric acid, HNO$_3$ for a minimum of 4 hours. Temperature of the acid is 120–150° F. The acid treatment converts the surface atoms to zirconium oxide and/or zirconium phosphate.
2. Rinse the wire segments with H$_2$O. Prepare a solution containing 7 mCi of Ce-144 as cerium nitrate solution. Do not add carrier. Adjust pH to 6.
3. Place the conditioned wire segments into the Ce-144 solution. Digest at 80–100° F. for 1 hour. Test the solution for activity. If more than 10% of the original Ce-144 remains in the solution, digest wires in the solution for 1 more hour.
4. Remove wires after loading the Ce-144 from the solution, rinse the wire segments with H$_2$O and dry.
5. Place each wire segment into an 0.011–0.012 inch diameter, 1.38 inch long heat shrink polyethylene terephthalate sleeve and heat to shrink the tubing around the radioactive section.
6. Insert the wire segment onto the catheter guide wire end using polyisocyanurate adhesive or laser weldment to seal the slip or friction fit joint.
7. Place a second sleeve over the wire segment and apply heat to shrink the sleeve. A high temperature laser or other heat source is used to seal the excess material at the end of the active length.

Example 10

Preparation of Ruthenium-106 IRCD by Coil Plating

I. Mounting of coil on spool.

Insert coil catheter wire distal end through holder spool nozzle, wind the catheter wire onto spool and secure with plastic cover.

Expose 3–4 inches length of coil was beyond spool nozzle.

Clamp assembly onto support to manipulate spool/wire coil during plating process. The coil is situated vertically.

II. Cleaning/activation of the coil.

Activate the coil as follows:
 a) Adjust power supply to 2.3 volts.
 b) Connect positive lead to platinum anode.
 c) Connect negative lead to top of catheter wire next to spool.
 d) Lower the spool assembly/wire was via the support clamp to immerse the coil into bath and activate at 12 milliamps average current for 6 minutes.
 e) Remove wire coil was from bath and rinse with $H_2O$.

III. Acid gold strike of wire coil

Prepare the plating bath as follows:
 a) Pipet 24 ml of Technic, Inc. acid gold strike solution into a clean 27 ml shell vial.
 b) Place a cylindrical platinum anode in the vial.
 c) Lower the spool assembly via the support clamp to immerse the coil to be plated into the bath.
 d) Stir the bath using a magnetic stir/heat plate and stir bar.

Apply the strike as follows:
 a) Adjust power supply to 2.3 volts.
 b) Connect positive lead to platinum anode.
 c) Connect negative lead to top of catheter wire.
 d) Lower wire into bath and plate at 15 milliamps for 4.5 minutes.
 e) Remove wire coil from bath, rinse with $H_2O$.

IV. Preparation of coil for ruthenium-106 plating

Apply several coats of Microshield masking agent to the coil to prevent ruthenium-106 from plating above the 2.8 cm length specified for the radioactive source length.

V. Plating of coil with ruthenium

Prepare the plating bath as follows:
 a) Pipet 300 microliters of ruthenium chloride stock solution containing 3.0 mg of ruthenium into a clean 50 ml beaker.
 b) Pipet 1.9 mCi of ruthenium-106 (0.182 ml volume) into the same beaker.
 c) Heat the combined solution gently at 60 degrees C. and evaporate to dryness to remove excess chloride
 d) Quantitatively transfer the solution to a clean 27 ml shell/plating vial situated in the shielded plating apparatus. Place the cylindrical platinum anode into the vial.
 e) Stir the bath using a magnetic stir/heat plate and stir bar.
 f) Pipe two 20 microliter start bath samples from the bath solution and transfer to 1 dram vials for assay of ruthenium-106 present at start of process.
 g) Heat the bath to approximately 60 degrees C. to convert the ruthenium chloride to ruthenium sulfamate.

Plate the coil as follows:
 a) Adjust the power supply to 2.3 volts initially.
 b) Connect the positive lead to the platinum anode lead.
 c) Connect the negative lead to the top of the catheter wire.
 d) Lower the wire coil via the clamp and immerse in the plating bath.
 e) Plate the coil for approximately 19 hours at an average current of 20 milliamps and 2.3–2.6 volts.
 f) Remove the coil from the plating bath, rinse with distilled $H_2O$ and store in a lead shield.
 g) Remove two 50 microliter aliquots from the plating bath and placed in dram vials for the stop bath assay.

VI. Ruthenium-106 plate conditioning

Remove the plated coil from the lead shield and sonicate for 7 seconds in a water bath to clean loose material off the coil surface.

Assay the water bath to determine the loss of radioactivity in this step.

VII. Plating of ruthenium coil with acid gold strike

Set up the plating bath as follows:
 a) Place a clean 27 ml shell vial into the shielded plating apparatus.
 b) Pipet 24 ml of commercial acid gold strike solution into the vial which is equipped with the cylindrical platinum anode.
 c) Lower the spool assembly via the support clamp to immerse the coil into the bath.
 d) Stir the bath using a magnetic plate and stir bar.

Apply the gold strike as follows:
 a) Adjust power supply to 2.1 volts.
 b) Connect positive lead to platinum anode.
 c) Connect negative lead to top of catheter wire near spool.
 d) Lower wire into bath and plate at 22 milliamps for 2.5 minutes.
 e) Remove wire coil from bath, rinse with $H_2O$ and transfer to a lead shield.

VIII. Overplating with Orosene hard gold

Apply the final protective plate using commercial hard gold plate as follows:
 a) Place a clean 27 ml shell vial into the shielded plating apparatus.
 b) Pipet 24.0 ml of Technic, Inc. supplied Orosene999 gold solution into into the vial and insert the cylindrical platinum anode.
 c) Stir the bath using a magnetic stir/heat plate and stir bar.

Perform the plating as follows:
 a) Set power supply voltage at 2.6 V.
 b) Set current initially at 5 milliamps.
 c) Connect the positive lead to the platinum anode.
 d) Connect the negative lead to the top of the catheter wire.
 e) Lower the coil/spool assembly to immerse the Ru-106 plated coil into the bath.
 f) Plate the source for approximately 40 minutes at 5 milliamps.
 g) Plate the source for another 20 minutes at 10 milliamps.
 h) Remove the source coil from the plating bath, rinse with distilled $H_2O$ and store in the lead shield.

IX Preliminary testing of the Ru-106 ICRD source

Perform wipe testing with methanol soaked Q-tips.

Place the catheter wire on the spool on the floor of the fume hood behind shielding and wipe according to the following sequence.
 a) First perform two cleaning wipes.
 b) Take wipes on the radioactive coil section, place into LSC mini-vials and count on a low background NaI(Tl) detector/scaler.
 c) Submit wipes in the vials to which 4 ml of Aquasol cocktail have been added, to the calibration lab for LSC counting to determine actual nanocurie values of these wipe samples.
 d) Confirm assay of the plating bath start bath and stop bath samples and mCi content of the wire coil source from calibration lab results.

Example 12
Preparation of a Ruthenium-106 ICRD By Plating

I. Mount coil on 0.007 mil (0.178 mm) diameter stainless steel mandrel.
  Clean mandrel with methanol.
  Mount a 0.4 inch (1 cm) section of 0.008 mil (0.2 mm) inner diameter polyimide on the mandrel.
  Mount the supplied 1.10 inch (26 mm) length of butt end welded platinum coil onto mandrel.
  Mount a 1.57 inch (4 cm) length section of polyimide tubing onto the mandrel, on top of the coil.

II. Activate and clean the mandrel
  Mandrel setup
    a) Slide the coil and long polyimide retainer sleeve 3 inches above the distal end of the mandrel to expose the bottom portion of the mandrel which supports the coil.
    b) Leave the 1 cm polyimide sleeve in place at distal end.
  Cleaning of mandrel
    a) Prepare a solution of 30% trisodium phosphate solution (TSP).
    b) Place 24 ml of TSP in a 27 ml shell vial equipped with a 1 inch diameter cylindrical platinum anode and heat to 50 degrees C.
    c) Stir the bath with heat/stir plate and magnetic stirrer.
    d) Heat bath to 50 degrees C.
    e) Connect the positive lead from the power supply to the anode.
    f) Connect the negative lead to the top of the mandrel wire.
    g) Lower the coil into the bath and clean the mandrel at 3.6 volts, 50 milliamps current for 30 seconds. Remove mandrel from plating bath and store in distilled $H_2O$.
  Activation of mandrel
    a) Prepare 75% $H_3PO_4$ solution with reagent $H_3PO_4$.
    b) Place 24 ml of 75% $H_3PO_4$ into a clean 27 ml shell vial equipped with a cylindrical platinum anode and heat to 50 degrees C.
    c) Connect leads to anode and mandrel wire as above.
    d) Lower coil assembly into the bath and activate the mandrel at 3.7 volts, 50 milliamps for 30 seconds.
    e) Remove coil assembly and store in clean distilled $H_2O$.

III. Activate/clean the coil mandrel assembly
  Coil assembly setup
    a) Slide platinum coil and polyimide retainer tubing down to distal end of mandrel.
    b) Rinse with methanol and dry.
    c) Mount the coil/mandrel assembly onto the retainer spool. Allow 4 inches of mandrel wire, including coil to extend beyond spool nozzle.
    d) Glue the polyimide tubing to the mandrel at the top with super glue (Loctite or Dow Corning) to secure the platinum coil in position.
  Cleaning and activation of coil mandrel assembly (as above in section II)
    a) Clean coil assemby with TSP at 3.4 volts, 50 milliamps current for 30 seconds.
    b) Clean assemby with 75% $H_3PO_4$ at 3.0 volts, 50 milliamps for 30 seconds.
    c) Remove source coil from bath and store in distilled $H_2O$.

IV. Plate coil with acid gold strike
  Pipet 24.0 ml of acid gold strike solution into a clean 27 ml shell vial and insert the cylindrical platinum anode.
  Stir the bath using a magnetic stir/heat plate and stir bar.
  Connect positive lead to the platinum anode and set power supply voltage to 0.5 volts.
  Connect the negative lead to the top of mandrel next to spool and immerse into bath, centering coil inside anode.
  Immediately increase voltage to 1.5 volts, then increase to 3.0 volts over 1 minute.
  Plate at 3.0 volts and 90–100 milliamps for 30 seconds.
  Remove from bath and store in distilled $H_2O$.

V. Plating of coil with ruthenium-106
  Prepare the plating bath as follows:
    a) Place a clean 27 ml shell vial into the shielded plating apparatus and insert an 0.5 inch diameter, 0.75 inch long cylindrical platinum electrode.
    b) Pipet 1.93 ml (15.6 mCi) of ruthenium-106 stock solution into a clean 50 ml beaker.
    c) Heat solution to near dryness at 60 degrees C. to remove excess chloride.
    d) Add 12 ml of sulfamate plating solution (pH 1.59) to the beaker dissolving the Ru-106 chloride.
    e) Transfer the Ru-106 sulfamate solution quantitatively into the plating vial.
    f) Rinse the 50 ml beaker with 15 ml of sulfamate plating solution and transfer quantitatively to the plating vial. Total bath volume is now 27 ml.
    g) Using the magnetic stir/heat plate and stir bar, stir the bath solution.
    h) Withdraw two 0.200 ml aliquots for the start bath assay.
    i) Heat the plating bath to 50° C. until the solution converts from brown to pale yellow (ruthenium converts from the chloride to the sulfamate).
  Plate the coil as follows:
    a) Place the spool/coil assembly into pneumatic clamp device.
    b) Connect the positive lead from the power supply to the anode.
    c) Connect the negative lead to the top of the mandrel next to the spool.
    d) Set the plating current to 14 milliamps maximum, voltage at 2.2 volts.
    e) Lower the coil remotely into the bath until it is vertically and radially centered versus the anode.
    f) Plate the coil with Ru-106 for 17 to 18 hours at 14 milliamps current and 2.2–2.3 volts.
    g) Remove source from plating bath and store in distilled water in a shielded vial.
    h) Remove two 1.0 ml stop bath samples for assay.

VI. Ruthenium-106 plate surface cleaning
  Ultrasonication cleaning
    a) Transfer the source to a sonication bath with the pneumatic clamp device.
    b) Sonicate for 1.5 minutes to remove residual bath contamination.
    c) Transfer the source back to its shielded location.
    d) Reserve the sonication bath for Ru-106 assay.
  Chemical cleaning and activation
    a) Set up the 27 ml bath containing 24 ml of trisodium phosphate (TSP) aand the cylindrical platinum anode in the shielded plating apparatus.
    b) Stir and heat to 50 degrees C.
    c) Transfer the source to the TSP bath and clean the source electrolytically at 3.1 volts, 50 milliamps current for 45 seconds.
    d) Remove source coil assembly from bath remotely and store in shielded vial containing distilled $H_2O$.

e) Set up the 75% $H_3PO_4$ activation bath in the shielded plating apparatus.
f) Stir and heat to 50 degrees C.
g) Transfer the source coil to the $H_3PO_4$ bath and activate at 3.0 volts, 50 milliamps current for 30 seconds.
h) Sonicate in distilled water for 1 minute.
i) Reserve sonication bath for Ru-106 assay.

VII. Plating of ruthenium-106 coil with acid gold strike
Set up the plating bath as follows:
a) Set up clean 27 ml shell vial in the shielded plating apparatus.
b) Insert the 1 inch diameter cylindrical platinum anode.
c) Pipet 24.0 ml of acid gold strike solution into the vial.
d) Stir the bath with the magnetic stirrer and stir bar.

Apply the gold strike as follows:
a) Set the power supply to 0.5 volts and connect the positive lead to the anode.
e) Transfer the source from the shield to above the plating bath and connect the negative lead to the top of the mandrel.
f) Lower the source coil into the plating bath, centering the coil vertically and radially versus the anode.
g) Immediately increase voltage to 1.5 volts then gradually ramp up the voltage to 3.0 volts over 1 minute.
b) Plate at 3.0 volts for 1 minute.
c) Raise source from bath and inspect against a black background to ensure that gold has plated over the ruthenium-106.
d) Transfer source coil assembly to shielded vial containing clean distilled $H_2O$.
e) Remove acid gold bath from shielded plating apparatus.

VIII. Orosene gold final overplate
Set up the hard gold overplate bath as follows:
a) Place a clean 27 ml shell vial into the shielded plating apparatus.
b) Pipet 24.0 ml of Technic, Inc. supplied Orosene999 gold plating solution into the vial and insert the 1 inch diameter cylindrical platinum anode.
c) Stir the bath with the magnetic stirrer and stir bar.

Perform the plating as follows:
a) Set the power supply voltage at 2.6 volts.
b) Set the current at 9 milliamps.
c) Transfer the source coil from the shield with the pneumatic clamp device to a location above the plating vial.
d) Connect the positive lead to the anode and the negative lead to the top of the mandrel.
e) Lower the source coil into the plating bath, centering the source vertically and radially with respect to the anode.
f) Plate for 20 minutes at 9 milliamps.
g) Remove from plating bath and transfer to shield.

IX Post cleaning of ruthenium-106 source.
Transfer the source coil from the shield to a sonication bath containing 0.1% Contrad-70 cleaning solution.
Sonicate for 2 minutes.
Sonicate source coil for 2 minutes in a bath containing distilled water.
Reserve sonication bath vials for assay of Ru-106.

X Source cleaning and cycle testing
Perform cycle test procedure per Guidant supplied protocol.
Perform wipe tests on wire coil after cycle testing to demonstrate that radioactive source surface is free of contamination (below 5 nanocuries).

Example 14

Preparation of Ruthenium-106 Catheter Guide Wire Source

This procedure defines the materials, techniques, and processes required to fabricate a sealed radioactive catheter guide wire source.

Safety Considerations

CAUTION: THE POTENTIAL FOR HIGH RADIATION EXPOSURE AND/OR CONTAMINATION EXISTS DURING THE FOLLOWING STEPS. GLOVES, LAB COATS AND ARM COVERINGS MUST BE WORN AND CAUTION EXERCISED WHILE PERFORMING THE PROCEDURE. THIS PROCEDURE IS TO BE PERFORMED BY PROPERLY TRAINED OPERATORS WHO WILL MINIMIZE RADIATION EXPOSURE TO THEMSELVES AND CO-WORKERS, WEAR AND/OR USE ALL APPROPRIATE DOSIMETRY AND SAFETY EQUIPMENT AND FOLLOW ALL RADIATION SAFETY PROCEDURES. IN PARTICULAR, THIS PROCESS MUST BE CONTINUALLY MONITORED FOR HIGH RADIATION FIELDS, CONTAMINATION ON HOOD LIPS AND OTHER SURFACES. WIPES SHALL BE TAKEN PERIODICALLY THROUGHOUT THE PROCESS AND COUNTED ON AN OPEN WINDOW GM DETECTOR, OR BY LIQUID SCINTILLATION IF A HIGHER COUNTING EFFICIENCY IS REQUIRED. WORK INVOLVING PRODUCTION QUANTITIES OF RUTHENIUM-106 GUIDE WIRE SOURCES SHALL BE PERFORMED IN A HOT CELL.

Radiation Characteristics

| Decay Mode: | Ru-106 | Beta Decay |
| --- | --- | --- |
| | Daughter Rh-106 | Beta, gamma decay |
| Half-life: | 366.5 days | |
| Principle Energies: | | |
| | Ru-106 Parent | |
| Beta: | 39.6 keV | 100% |
| | Rh-106 Daughter | |
| Beta: | 3.55 MeV | 67.2% |
| | 3.1 MeV | 11.3% |
| | 2.44 MeV | 12.3% |
| | 2.0 MeV | 3.1% |
| Gamma: | 0.512 MeV | 19.1% |
| | Others | |

Source of Radioactivity

The Ru-106 is produced by neutron fissioning of uranium-235 in a reactor and is processed from spent uranium fuel rods. The processed nuclide is purchased through Chemotrade (Russia).

7.0 Equipment and Materials
7.1 Equipment
7.1.1 Portable GM detector, Ludlum Model #3 or equivalent
7.1.2 Mini-heat/stir plates
7.1.3 D. C. Power Supply, Hewlett Packard 3012A, or equivalent
7.1.4 0-250 microliter Pipetman with 10, 100 microliter tips
7.1.5 Calibrated Sartorius balance, or equivalent, 0.1 mg sensitivity,
7.1.6 Capintec Ion Chamber, calibrated
7.1.7 Custom Lead-plexi plating vessel shield/hot plate assembly and vial tops 7.1.8 Peristaltic pump and tubing
7.1.9 Pneumatic Clamp Drive System
7.1.10 Custom wire coil spool assembly
7.1.11 Custom Lead-plexi shields for C-cones
7.1.12 Microscope with Polaroid camera adaptor
7.1.13 Polaroid camera for microscopy
7.2 Materials
7.2.1 1 ml pipetor, plunger type
7.2.2 Beakers, 50, 100, 250, 400 ml sizes
7.2.3 Watch glass covers
7.2.4 1, 5, 10 ml poly pipets
7.2.5 Pipetor bulb
7.2.6 Poly bottles, 60, 125 ml sizes
7.2.7 Poly transfer pipets
7.2.8 12 inch tongs
7.2.9 1 dram vials and screw caps
7.2.10 Lead and lead glass shielding
7.2.11 Platinum anodes, cylindrical, 1.25 and 2.5 cm diameter, 2.0 cm height
7.2.12 pH narrow range paper, 1–2.5
7.2.13 Magnetic stir bars, $\frac{1}{8}"\times\frac{1}{2}"$
7.2.14 Vinyl, latex tubing
7.2.15 Ring stand with clamps
7.2.17 Q-tips
7.2.18 50 ml poly centrifuge cones
7.2.19 Poly weigh boats
7.2.20 12, 16, 20, 27 ml shell vials and caps
7.3 Chemicals
7.3.1 Sulfamic acid/sodium sulfamate solution, 45–50 grams per liter, pH 1.50–1.80.
7.3.2 Reagent grade methanol
7.3.3 Technic acid gold strike, or equivalent, 0.25 troy oz. per gallon
7.3.4 6 M HCl
7.3.5 Milli-Q water or equivalent
7.3.6 Ruthenium carrier solution
7.3.7 Ruthenium-106 nuclide, stocked in 6–8M HCl
7.3.8 Technic Orosene999 gold plating solution, 1 troy oz. per gallon
7.3.9 Aquasol® LSC cocktail
8.0 Fabrication of Ruthenium-106 Coil
8.1 Setup of Coil Assembly
8.1.1 Check the model number, design and dimensions of the wires and coils to ensure that they are correct.
8.1.2 CAREFULLY inspect the mandrel and coils. The last 6 cm of mandrel wire tip must be straight, with no kinks or sharp bends. The coils must be tightly wound, with no gaps or deformed segments.
8.1.3 Examine the coil tip section under a microscope at 30×. The coil should be straight with coil turns spaced uniformly, with no kinks or deformation. The finish should appear very shiny and smooth.
8.2 Cleaning and Activation of Wire Coil
8.2.1. Place a 1 cm length of 7.5 mil I. D. polyimide tubing onto the mandrel and position next to the end ball on the mandrel. Next, slide on the platinum/nickel coil onto a 7 mil diameter mandrel wire. Finally, slide on an 8–10 cm length of 7.5–8 mil I.D. polyimide tubing above the coil. Slide the coil and long polyimide tubing up at least 4 cm away from the polyimide sleeve next to the end ball on the mandrel for the following cleaning steps, 8.2.2–8.2.4.
8.2.2 Rinse the mandrel and coil with methanol. Place the mandrel in a 27 ml shell vial which contains 8 grams of trisodium phosphate dissolved in 24 ml $H_2O$, heated to 50° C. Support the mandrel with a small clamp.
8.2.3 Attach the red lead (+) to the anode and the black lead (−) to the mandrel. Cathodically clean the mandrel at a current of 50 milliamps for 30 seconds. Rinse the mandrel with milli-Q $H_2O$.
8.2.4 Put 24 ml fresh 75% $H_3PO_4$ solution in a clean 27 ml shell vial and heat the bath to 50° C. Insert a clean 1" diameter platinum anode. Attach the red lead (+) to the anode and the black lead (−) to the mandrel.
8.2.5 Lower the mandrel into the bath and cathodically activate the mandrel at 50 milliamps for 30 seconds. Remove and rinse the mandrel with milli-Q $H_2O$.
8.2.6 Slide the platinum coil to its plating position on the mandrel, butted up against the polyimide sleeve section next to the end ball. Using super glue, secure the top of the long polyimide tubing to the mandrel.
8.2.7 Rinse the coil with methanol, dry and set up the assembly in the trisodium phosphate plating bath configuration as in 8.2.2 and heat to 50° C. Attach the red (+) lead to the platinum anode and the black (−) lead to the mandrel. Cathodically clean the coil at 3.0 volts for 1 minute. Remove and rinse thoroughly with milli-Q $H_2O$.
8.2.8 Prepare a 75% $H_3PO_4$ in a 27 ml shell vial with a mini stir bar and platinum anode. Attach the red lead (+) to the anode and the black lead (−) to the mandrel. Cathodically activate the coil at 3.0 volts in the 75% $H_3PO_4$ heated to 50° C. for 1 minute.
8.2.9 Remove and rinse the coil with milli-Q $H_2O$ and store in vial containing milli-Q $H_2O$.
8.2.10 Apply 6 coats of Micro-shield to the end ball to seal the stainless steel surface. Allow to cure (1 minute each coat) and rinse the coil assembly with milli-Q $H_2O$ and store in fresh milli-Q $H_2O$.
8.2.11 Obtain a spool assembly, remove the allen screw and plastic boot. Insert the proximal end of the mandrel to be plated through the hole in the spool nozzle from the front aperture. Draw the mandrel through the nozzle, leaving 4 inches of mandrel tip length (and coil) exposed beyond the spool nozzle.
8.2.12 Holding the wire with your index finger against the spool where it enters the hole, tightly roll the guide wire or guide wire coil onto the spool.
8.2.13 While holding the wound coil securely, slip the plastic boot onto the spool, with the other end of the guide wire passing through the allen screw center hole. Secure with the allen screw. Leave about 1–2 inches of wire protruding through the spool cover screw hole.
8.2.13 Store the wound mandrel/coil in the clean milli-Q $H_2O$ to keep surface wet.
8.3 Electrodeposition of Acid Gold Strike on the Coil
8.3.1 Prepare acid gold strike bath by dispensing 12.0 or 24.0 ml of Technic acid gold strike solution into a clean 10 or 27 ml shell vial. Insert a clean platinum cylindrical anode, ½" diameter, ¾×" coil length, and a clean $\frac{1}{8}"\times\frac{1}{2}"$ mini-stir bar. Clamp bath over the stir plate. Heat bath to a temperature of 50° C.
8.3.2 Clamp the wire assembly/spool above the plating bath. Connect the black lead (−) to the mandrel end and the red lead (+) to the platinum anode lead.
8.3.3 Adjust the power supply to a setting of 0.5 volts. Lower the clamp, inserting the wire tip through the center hole in the bath cover to within ⅛" of the top of the magnetic stir bar. Turn the magnetic stirrer to a setting of 2.5–3. The wire tip must be centered versus the platinum anode vertically and laterally.
8.3.4 Increase voltage slowly to 1.5 volts over 30 seconds, then increase voltage to 3 volts. Plate for 60 seconds.
8.3.5 Remove wire spool assembly from strike bath. Note color, the wire should be a bright gold color. Rinse the wire tip with $H_2O$ and store in milli-Q $H_2O$.

8.3.6 Examine the coil under the H1104 microscope at 30 power. Record observations. The gold strike should be perfectly smooth and shiny. There should be no nodules, projections or voids in the plate. DO THIS ON COLD OR TRACE LEVEL PROTOTYPES ONLY!
NOTE: If wires are not immediately plated with radioruthenium, store the mandrel/coil assembly in Milli-Q water.

8.4 Preparation of Ruthenium 106 for Electrodeposition 8.4.1 Transfer required amount of Ru-106, +20%, to a 1 dram vial and assay in the CRC12R calibrated Capintec ion chamber in H1111. This assumes ~80% plating yield.
CAUTION: Use 2" lead glass shielding and 12" tongs to mimimize body and hand exposure.

8.4.2 Set up a clean 10 or 27 ml shell vial as the plating bath and place a mini-stir bar and platinum coil anode in the vial. The length of the anode coil is 1.9 cm (¾"), diameter is 1.25 cm (½"); it must be vertically and laterally centered in the vial. Dispense 8.0 or 24.0 ml $H_2O$ into vial and mark a line on the vial at the meniscus. Discard the water.

8.4.3 Place the vial inside of the plating jig assembly. The mandrel (proximal) end should extend about 1–2" beyond the assembly cover.

8.4.4 Place the inlet line of the pumping system into the assay vial containing the Ru-106. Place the outlet line in a clean 50 ml beaker.

8.4.5 Transfer the Ru-106 into the beaker from the assay vial using the Master Flex peristaltic pump and tubing. Add 3 ml of 6M HCl to the dram vial and transfer this rinse into same beaker with the pump. Shield beaker using lead/plexi or lead glass.

8.4.6 Repeat rinse as in 8.4.5, transferring to the same beaker. Read empty vial on Ludlum Model 3 with beta window open. If reading exceeds 300 mr/hr on the Ludlum Model 3, beta window open, perform one more rinse, transferring to the 50 ml beaker.

8.4.7 Place the beaker containing the Ru-106 on a mini hot plate and evaporate the Ru-106 solution to near dryness at a setting of "3–3.5". Dispense 3.0 ml or 12.0 ml of sulfamic acid into a 50 ml C-cone and transfer it with the peristaltic pump into the beaker to convert the Ru-106 to ruthenium sulfamate. Allow $RuCl_3$ to completely dissolve.

8.4.8 Insert outlet tubing through the plating vial cap opening and transfer the dissolved Ru-106 into the plating cell with the peristaltic pump.

8.4.9 Pipet a 3.0 ml or 6.0 ml portion of sulfamic acid solution into the beaker for rinsing, depending on the plating vial size. Transfer the rinse to the plating cell with the peristaltic pump.

8.4.10 Repeat the rinse step with a second 2.0 ml or 6.0 ml fraction of sulfamic acid. Transfer it to the plating cell. The total volume in the plating cell is either 8.0 ml or 24.0 ml.

8.4.11 Check the volume transferred to the plating vial; it should be at the 8.0 or 24.0 level marked on the vial. If not, add sufficient sulfamic acid to bring level to mark.

8.4.12 Check the beaker for residual activity with the Ludlum Model #3 detector; it should read less than 500 mr per hr.

8.5 Electrodeposition of Ruthenium-106 onto the Coil 8.5.1 Stir the ruthenium-106 sulfamate solution in the shell vial on the stir/heat plate for 1–2 minutes. Remove two 50 or 200 microliter samples from the bath after stirring, using a Pipetman with a ½" lead/plexi hand shield. Access the solution through the tubing port in the cap. Use 1 dram black top vials for the samples.
NOTE: Do not remove more than 50 microliter volumes from the 11 ml plating bath!

8.5.2 Assay the samples on the Cal lab Capintec S/N 12819 ion chamber in H1111 at a fixed geometry. Use the dial-in factor posted for Ru-106. The dial-in factor used was 48. Record results of the assay for both samples.

8.5.3 Mount the spool assembly in the pneumatic clamp with the tip pointing straight down and the other end of the wire pointing away from the clamp. Secure the spool with the pneumatic clamp and then insert the wire coil segment through the center hole to a depth of 3.5 cm, or ⅛" above the magnetic stir bar. Adjust the wire and electrode so that the wire coil tip section is centered. The end of the wire coil is about ⅛" below the bottom of the anode.
NOTE: These distances are estimates and done by eye through the lead glass shield.

8.5.4 Adjust the heat setting to "2.5" on the hot plate which corresponds to a temperature of ~50° C. Adjust the stir bar setting to "2.5–3". Make sure that the stir bar does not contact the coil tip.
NOTE: These hot plates have been previously tested for temperature pot settings using a thermometer.

8.5.5 Attach the red (+) lead to the platinum electrode. Attach the black (–) lead to the mandrel wire end. Adjust the power supply current to 14 milliamps-constant. Carefully lower the wire/coil into the plating bath with the pneumatic device. The end of the coil should be ⅛" to ¹⁄₄₀" below the bottom of the anode. Plate for 18 hours (overnight). Record start and stop times.

8.5.6 After plating is complete, remove 2×1.0 ml samples from the bath and count on the H1111 CRC12R calibrated Capintec ion chamber in the same geometry as the start bath samples. Compare to the starting bath sample. If >80% of the Ru-106 is plated, stop. If <80%, plate for 1–2 more hours.

Calculate the percent plated using the formula:

[(Cts. start bath–Cts stop bath)/Cts. start bath]×100

[(_–_)/_]×100=_% plated.

8.5.7 Lift the spool/coil assembly from bath with pneumatic drive, retract to left and rotate drive unit 45°. Carefully lower the source into a pre-positioned F shield which contains a 27 ml shell vial filled with milli-Q $H_2O$. Hold spool with 12" tongs, release pneumatic clamp and lower spool onto shield neck which supports the source spool.

8.5.8 Insert inlet poly line through port in cap to the bottom of the plating vial. Place outlet poly line into shielded waste container. Using the peristaltic pump, transfer the bath solution to hot waste.

8.5.9 Next, place the waste outlet line into a C-cone containing 27 ml of $H_2O$ and reversing the peristaltic pump, transfer the $H_2O$ into the plating bath vial. Move outlet line from plating cell to low level waste, reverse pump, and pump rinse to low level waste container.

8.5.10 Remove the empty rinsed Ru-106 plating bath and anode from the plating jig/shield and place in lead shield.

8.5.11 Place the ultrasonic bath with top shield on platform next to the plating jig. Using pneumatic clamp arrangement, move the wire coil from the F pig into a 20 ml shell vial filled with 0.1% Contrad-70 cleaning solution positioned in the ultrasonic bath. Submerge the tip section and sonicate the bare Ru-106 coil for 1 minute.

8.5.12 Transfer the coil source back to the F pig containing a clean 27 ml shell vial filled with milli-Q $H_2O$ with the pneumatic device. Remove the sonication vial, cap it, place an into a ½" shield, bag and assay on the H1111 Capintec CRC12R ion chamber . . . The dial-in factor used was 48.

8.5.13 Place 20 ml shell vial containing milli-Q $H_2O$ into the sonication bath. Transfer source coil pneumatically from F shield to the bath. Sonicate for 1 minute. Return source coil to the F pig. Cap the 2nd sonication vial, wipe, bag and assay as in step 8.5.12.

8.5.14 Place a third 20 ml shell vial filled with milli-Q $H_2O$ in the sonication bath. Transfer souce coil to the sonication bath pneumatically and sonicate for 1 minute. Return source coil to the F shield/water reservoir. 8.5.15 Cap the 3rd sonication vial, wipe, bag and assay as in step 8.5.11.

8.5.16 Place a 27 ml shell vial which contains 8 grams of commercial trisodium phosphate dissolved in 24 ml $H_2O$ and a 1" diameter platinum electrode, into the plating jig and heat to 50°0 C. Set the magnetic stir speed to 2–2.5.

8.5.17 Attach the red lead (+) to the anode and the black lead (−) to the mandrel. Transfer the coil source from the F shield to the plating bath. Cathodically clean the plated coil at a current of 50 milliamps for 30 seconds. Return the coil source to the F shield containing a clean 27 ml vial of milli-Q $H_2O$.

8.5.18 Put 24 ml fresh 75% $H_3PO_4$ solution in a clean 27 ml shell vial and heat the bath to 50° C. Insert a clean 1" diameter platinum anode. Adjust the stir speed to 2–2.5 if necessary. Attach the red lead (+) to the anode and the black lead (−) to the mandrel.

8.5.19 Pneumatically transfer the Ru-106 coil to the plating bath and cathodically activate the coil source at 50 milliamps for 30 seconds. Return the coil to the F shield. Dispose of the bath to low level waste container.

8.6 Electrodeposition of Acid Gold Strike on Ruthenium-106 Plated Guide Wire 8.6.1 Place a clean 10 or 27 ml shell vial containing 8 or 24 ml pre-heated acid gold strike and anode into the plating jig/shield. Set stirrer at 2–2.5.

8.6.2 Connect red lead to anode and black lead to distal end of mandrel wire. Set the voltage at 0.5 volts, then transfer source coil from F pig into plating cell with pneumatic device.

8.6.3 Increase voltage slowly over 1 minute to 1.5 volts. Finally, increase voltage to 3 volts over 1 minute and hold for 60 seconds. Stop plating after 60 seconds.

8.6.4 Tape a piece of black paper on back hood wall directly behind plating jig. Raise source coil out of plating bath, and inspect through the lead glass shield. Against a black background it will appear gold in color.

8.6.5 Return source coil to the F shield containing a clean 27 ml vial of milli-Q $H_2O$.

8.6.6 Transfer the coil source from the F shield into the sonication bath containing 0.1% Contrad-70 solution in a 5 dram (20 ml) vial. Sonicate for 2 minutes to clean trace particulate contamination from the coil and mandrel. Transfer the source back to the F shield.

8.6.7 Cap the sonication vial, remove from bath, wipe, bag and assay on the H1111 Capintec CRC12R ion chamber. Record reading.

8.7 Electrodeposition of Final Gold Plate on the Guide Wire 8.7.1 Add 8.0 or 24.0 ml of OROSENE 999 gold plating solution to a clean plating vial. Turn stir motor to 2–2.5 speed so that the stir bar is turning very slowly. The stir plate motor will provide sufficient heat.

8.7.2 Adjust the power supply voltage setting to 2.6 volts. Connect the red (+) lead to the anode and the black lead (−) to the mandrel. Lower the coil into the bath with the pneumatic clamp and plate at a current of 6 to 10 milliamps for 15 to 30 minutes, depending on thickness of overplate desired. This plating time and current should deposit 0.1 to 0.2 mils (0.0001 to 0.0002 inches) of gold plate.

8.7.3 Turn off power supply and stir/heat plate, disconnect leads and pneumatically raise the wire/spool assembly. Inspect the wire tip section through the lead/plexi shield against the black background. It should be bright gold.

8.7.4 Sonicate the completed wire in a clean 20 ml shell vial filled with 0.1% Contrad-70 for 1 minute. Transfer the source to the F shield containing clean milli-Q $H_2O$ in a 27 ml shell vial.

8.7.5 Cap the sonication vial, wipe, bag and submit for assay on the H1111 Capintec CRC12R. Record reading.

8.7.6 Place a 20 ml shell vial filled with $H_2O$ in the ultrasonic bath. Transfer the coil source to the bath and sonicate for 1 minute. Remove the coil source to the F shield.

8.7.7 Cap the sonication vial, wipe, bag and submit for assay on the H1111 Capintec CRC12R. Record reading.

8.7.8 Ion chamber the gold plated Ru-106 coil source in the H1111 CRC12R ion chamber at the approved dial setting. The dial setting used was 24. Record reading.

8.8 Preparation for Mandrel Transfer and Cycle Testing 8.8.1 Prior to the transfer of the coil source to the mechanical transfer hood, the following preliminary wipe testing should be conducted. Four cleaning wipes using Q-tips soaked in methanol, then 4 final wipes on either side of the coil section are performed. The wipes are submitted for LSC and counts recorded. If any wipe exceeds $5 \times 10^{-3}$ microcuries, further cleaning must be performed.

8.8.2 Perform wipe tests on the cold wire mandrel surface. If contaminated, these surfaces must be cleaned until wipe results are below $1 \times 10^{-3}$ microcuries.

8.7.3 The final wipes are submitted in LSC mini-vials with 4 ml of cocktail. Complete Analytical Request Form and submit to Calibration lab with vials.

8.8.4 Transfer the F shield containing the finished source to the mechanical transfer hood for the mandrel to mandrel transfer.

8.8.5 Perform stress testing on sample wire(s) using the heart model system cycle.

Utility

The following are considered advantages of using Ce-144 or Ru-106 in an ICRD) compared with an ICRD containing Co-57 or Ir-192.

a) With Ce-144 or Ru-106, only about 5–10 mCi are necessary to deliver the required radiation dosage at 1 and 4 mm in the artery at the proper 4:1 ratio, as compared with 1300 to 2300 mCi of Co-57, or 100 mCi of Ir-192. Thus, the efficacy of this approach is superior in terms of optimizing target dose.

b) Photon emitters such as Co-57 or Ir-192 deliver substantial dose outside the patient to the attending physician or the technologists, requiring that they wear cumbersome shielding or exit the cath lab. External dosage for Ce-144 or Ru-106 is estimated at just 0.5 to 5 mR at a 30 cm distance from the wire source location for a 15 minute exposure. External dosage is calculated to be in excess of 200 mR for Ir-192 at the same distance from the wire source.

c) With Ce-144 or Ru-106, much less dosage is delivered to surrounding healthy tissue or organs, compared to the dosages delivered by Co-57 or Ir-192. The high abundance 122 keV to 468 keV photons emitted by the latter nuclides are much more penetrating, therefore they interact very inefficiently at the 1 to 4 mm distances, depositing much more of their energy in more distant parts of the anatomy. Conversely, the strong beta particles of up to 3 to 3.5 MeV in energy emitted by the Ce-144 or Ru-106 interact almost totally in the target 1 to 4 mm range where the plaque and arterial tissue are located.

d) In comparison to Sr-90 which emits a 2.2 MeV beta particle, the more penetrating 3–3.5 MeV beta particles of Ce-144 or Ru-106 have greater range suffient to penetrate to the outer arterial wall, whereas the weaker Sr-90 beta provides a less than optimal dosage ratio to maintain the 4:1 ratio at 1 mm and 4 mm. Therefore more activity is required, potentially overdosing the endothelial wall tissue in smaller arteries. Further, the demonstrated toxicity of 29 year half-life Sr-90 as a bone seeker is well documented; should the source rupture, the nuclide could locate in the patient's bone tissue, resulting in significant dose to the bone marrow.

e) The long half lives of Ce-144 (285 days) and Ru-106 (1.02 years) permit extended usage (reusable sources) of the present intra-coronary radiation devices, as compared to a device containing Ir-192, which has just a 74 day half life.

The following are considered advantages of using Ce-144 or Ru-106 in an ICRD compared with an ICRD containing P-32. Phosphorus-32, a beta emitter with a 1.7 MeV end point energy is also being employed in an ICRD. This methodology utilizes a catheter balloon which is filled with a saline solution of the P-32 nuclide. The disadvantages of this approach are: (a) the beta energy may not be sufficient to provide the optimal dosage at the 4–6 mm distance, especially if the artery contains calcified plaque; (b) the potential for leakage of nuclide from a balloon into the patient's blood stream is higher than with a solid sealed wire source; and (c) short half-life (14 days) of P-32 means that sources manufactured from this radionuclide cannot be reused or are disposable which make them much more expensive.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A device for intra-coronary radiation therapy, comprising;
   (a) a wire;
   (b) a radiation source deposited or absorbed onto the wire, wherein the radiation source is Ce-144 or Ru-106; and,
   (c) a first biocompatible material scaling the radiation and wire.

2. A device according to claim 1, wherein the radiation source is Ru-106.

3. A device according to claim 1, wherein the radiation source is Ce-144.

4. A device according to claim 1, wherein the wire is metal and is selected from: zirconium, titanium, aluminum, nickel, copper, graphite wire, 304 stainless steel or copper plated stainless steel.

5. A device according to claim 4, wherein the wire is 304 stainless steel or copper plated stainless steel.

6. A device according to claim 1, wherein the first biocompatible material is selected from: polyimide, polyamide, polyvinyl chloride, gold, nickel, and heat shrink tubing.

7. A device according to claim 6, wherein the first biocompatible material is heat shrink tubing.

8. A device according to claim 7, wherein the first biocompatible material is polyethylene terephthalate.

9. A device according to claim 1, wherein a second biocompatible material encapsulates the intra-coronary radiation device attached to the guide wire.

10. A device according to claim 9, wherein the second biocompatible material is heat shrink tubing.

11. A device according to claim 10, wherein the second biocompatible material is polyethylene terephthalate.

12. A device for intra-coronary radiation therapy, comprising:
    (a) a wire, wherein the wire is an extruded wire, comprising:
       (ai) a radiation source selected from Ce-144 and Ru-106; and,
       (aii) a metal selected from copper, aluminum, sliver, gold and nickel.

13. A device according to claim 12, wherein the radiation source is Ce-144 and the metal is aluminum.

14. A process for making an intra-coronary radiation device, comprising:
    (a) depositing a radioactive source onto a metal wire segment, wherein the radioactive source is Ce-144 or Ru-106; and,
    (b) sealing the deposited radioactive source with a first biocompatible material.

15. A process according to claim 14, wherein the radiation source is Ru-106.

16. A process according to claim 14, the radiation source is Ce-144.

17. A process according to claim 14, wherein the radioactive source is deposited onto the metal wire by electrolytic means.

18. A process according to claim 14, wherein the radioactive source is deposited onto the metal wire by an oxidative-reductive process.

19. A process for making an intra-coronary radiation device, comprising;
    (a) absorbing a radioactive source onto a metal wire segment, wherein the radioactive source is Ce-144 or Ru-106: and;
    (b) sealing the deposited radioactive source with a first biocompatible material.

20. A device for intra-coronary radiation therapy, prepared by the process comprising the steps of:
    (a)
    (b) depositing, or absorbing, a radiation source onto a wire, wherein the radiation source is Ce-144 or Ru-106; and
    (c) sealing the radiation source and wire with a first biocompatible material.

21. A new device according to claim 20, wherein depositing the radiation source is by electrolytic means.

22. A device according to claim 20, wherein depositing the radiation source is by an oxidative-reductive process.

23. An apparatus for intra-coronary radiation therapy comprising a device according to claim 1 and a guide wire, wherein the device is attached to the guide wire, and the guide wire is capable of being inserted into a catheter.

* * * * *